United States Patent [19]

Harada

[11] Patent Number: 5,235,862
[45] Date of Patent: Aug. 17, 1993

[54] SAMPLE HANDLING METHOD AND APPARATUS FOR ATOMIC ABSORPTION ANALYSIS

[75] Inventor: Katsuhito Harada, Katsuta, Japan

[73] Assignee: Hitachi, Ltd., Tokyo, Japan

[21] Appl. No.: 731,867

[22] Filed: Jul. 18, 1991

[30] Foreign Application Priority Data

Jul. 19, 1990 [JP] Japan ................... 2-191445

[51] Int. Cl.$^5$ ............................. G01N 21/74
[52] U.S. Cl. ................. 73/863.11; 356/312; 436/157; 436/159
[58] Field of Search ......... 73/863.11, 863.12; 436/157, 159, 174; 356/312

[56] References Cited

U.S. PATENT DOCUMENTS

| Re. 33,007 | 8/1989 | Bier | 73/863.12 X |
| 4,267,953 | 5/1981 | Hoffman et al. | 228/118 X |
| 4,806,489 | 2/1989 | Beach | 436/82 |

FOREIGN PATENT DOCUMENTS

| 45991 | 4/1977 | Japan | 73/863.11 |
| 64592 | 9/1978 | Japan . | |
| 55440 | 3/1988 | Japan . | |
| 13437 | 1/1989 | Japan . | |
| 398858 | 9/1973 | U.S.S.R. | 73/863.11 |
| 2104656 | 3/1983 | United Kingdom . | |

OTHER PUBLICATIONS

"Atomic Absorption Analysis with the Graphite Furnace Using Matrix Modification"; *Atomic Absorption Newsletter* vol. 14, No. 5; Sep.-Oct. 1975 pp. 127-130; Richard D. Ediger.

*Primary Examiner*—Tom Noland
*Attorney, Agent, or Firm*—Antonelli, Terry, Stout & Kraus

[57] ABSTRACT

A sample handling apparatus includes a furnace which atomizes elements to be tested in a sample. A matrix modifier is added to the furnace. A quantity of the sample is subsequently added to the furnace. An additional quantity of the matrix modifier is then added into the furnace. The furnace is heated to atomization temperature to permit analysis of the sample to be tested.

12 Claims, 4 Drawing Sheets

SAMPLE HANDLING METHOD AND APPARATUS FOR ATOMIC ABSORPTION ANALYSIS

BACKGROUND OF THE INVENTION

1. Field of the Invention

The present invention relates to a sample handling method and apparatus for atomic absorption analysis, more particularly, to a sample handling method and apparatus for atomizing elements to be tested in a sample by using a graphite furnace.

2. Description of the Related Art

An example of an atomic absorption analysis method is a method for atomizing a sample within a tubular graphite furnace. To reduce measurement errors concerning elements to be tested in such an analysis, matrix modifiers are often mixed with samples.

Shown in a U.S. Pat. No. 4,517,850 (corresponding Japanese Patent Laid-Open Publication: 58-92839) is a case where a blank solution, a matrix modifier solution, a standard solution, and a sample solution are sucked into a nozzle one after another in this order and this series of ingredients are discharged into a tubular furnace.

Although the method of the prior art can automatically dispense a sample and a matrix modifier into an atomizer furnace, there is a problem in that the sample and matrix modifier are not sufficiently mixed with each other in comparison with a preliminary mixing method by hand.

SUMMARY OF THE INVENTION

An object of the present invention is to provide a sample handling method and apparatus for atomic absorption analysis which is capable of obtaining the reproducibility of measured values comparable to those of the preliminary mixing method by hand.

Another object of the present invention is to provide a sample handling method and apparatus for atomic absorption analysis which is capable of increasing the sensitivity for measuring low-concentration elements in a sample.

The present invention is characterized in that a matrix modifier is put into a furnace prior to the addition of the sample into the furnace, and in that, after the addition of the sample, a matrix modifier is further added into the furnace.

In a preferred embodiment of the present invention, after a matrix modifier is added into the deposition zone inside an atomizer furnace, the sample solution is added into the deposition zone in succession. As a consequence, the sample is distributed over the layers of the matrix modifier on the deposition zone, and a part of the sample enters the matrix modifier of the lower layers. Therefore, the quality of the contact between the matrix modifier and the sample is excellent. As the result of the addition of the matrix modifier into the deposition zone following the addition of the sample, a part of the matrix modifier enters into the sample layer.

As a result, there occurs a state in which the sample is sandwiched or enclosed between a lower layer and an upper layer of the matrix modifier. Therefore, the contact between the sample and the matrix modifier improves to a degree equivalent to a case in which the preliminary mixture is done by hand. Thereafter, if the furnace is heated to high temperatures to atomize elements to be tested in the sample, atomized vapor suitable for absorption photometry can be obtained.

A standard solution and a blank solution may be added to the sample in the deposition zone of the furnace. By adding additional matrix modifiers on these layers, the sample, the standard solution and the blank solution can be held substantially in a sandwiched form by the matrix modifiers.

When the concentration of the elements in the sample being tested is extremely low, it is expedient that the most possible sample is supplied to the deposition zone of the furnace. However, there is generally an upper limit in the volume of the liquid sample which can be maintained in the deposition zone.

In the present invention, when the most possible sample is supplied, and after the matrix modifier solution previously added is dried, for example, 0.10 ml of sample solution is added and dried. Thereafter, the further addition and drying of sample solutions of 0.10 ml each are repeated. Thus, the sample is accumulated so that the total volume of the sample on the deposition zone is reduced and the absolute quantity of the elements being tested is increased. When the addition of a sample is repeated in the above way, a matrix modifier is also added during the process.

When an additional matrix modifier solution is added onto the dried laminate of matrix modifiers and samples, which have been previously added, the solution of the matrix modifier is liable to permeate the dried substance.

The furnace is maintained at a temperature lower than an ashing temperature while the matrix modifier and the sample are being added and dried. The furnace is heated to an ashing temperature and then heated to an atomization temperature after all of the ingredients has been completely added.

DETAILED DESCRIPTION OF THE PREFERRED EMBODIMENTS

An embodiment of the present invention will be explained below with reference to FIGS. 1 through 4.

First, the construction of an atomic absorption analysis apparatus shown in FIG. 1 will be explained. This analysis apparatus comprises an atomic absorption spectrophotometer, a graphite atomizer section, an automatic sampler section, and a computer that controls the operation of each of the sections and performs data processing.

Figure 1:
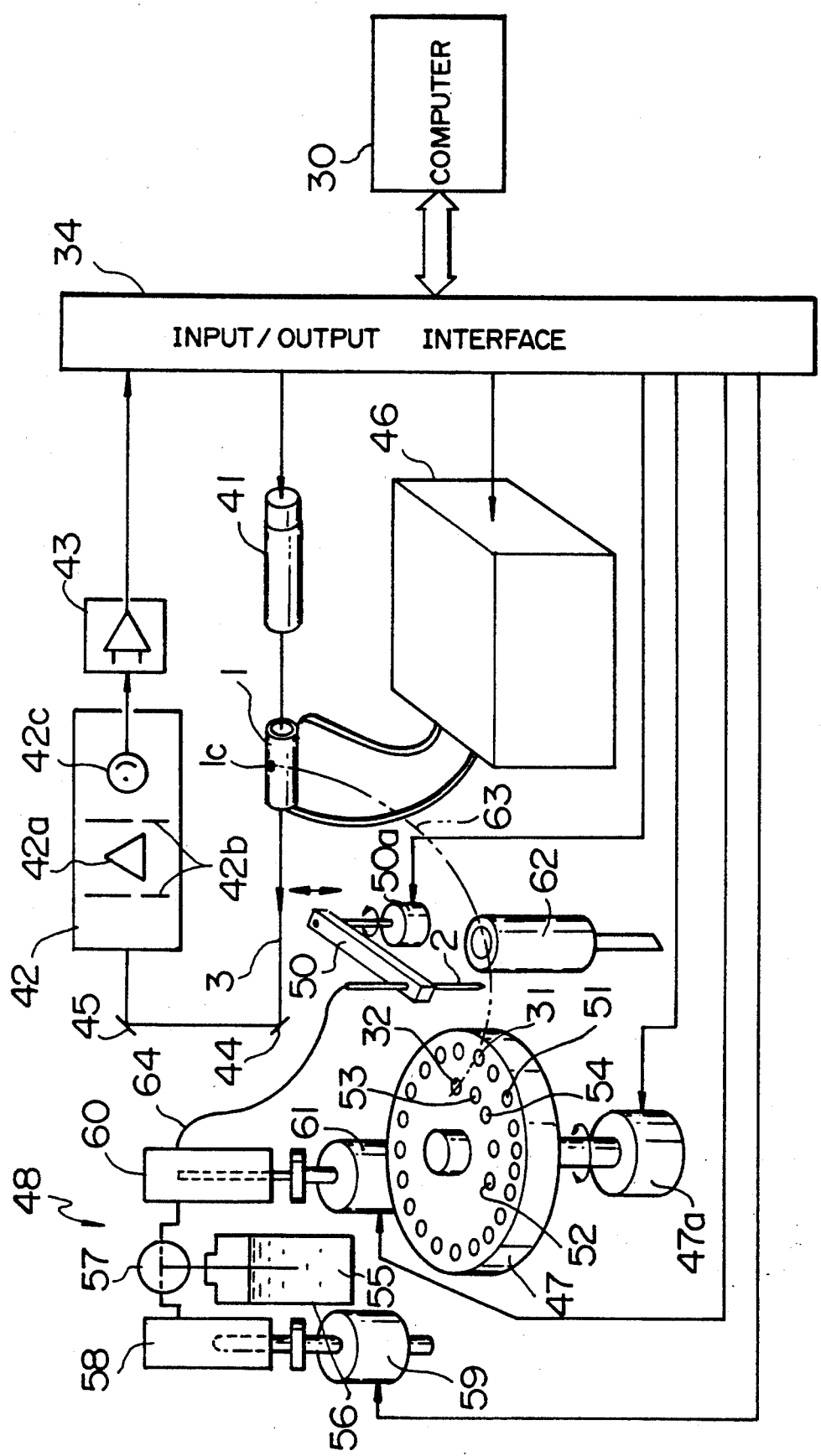
FIG. 1 is a schematic view showing the entire construction of an apparatus of an embodiment in which the present invention is applied.

In FIG. 1, the atomic absorption spectrophotometer comprises a hollow cathode lamp 41, a monochrometor 42, and a signal amplifier 43 and is set in a ready condition in which measurements can be made at any time. The hollow cathode lamp 41 is lit when a lighting driving current is supplied via an input/output interface by a command from a computer 30. A light ray 3 emitted from the hollow cathode lamp 41 passes through the inside of the tubular graphite furnace 1, and enters the monochrometor 42 after it is guided by reflection mirrors 44 and 45. The monochrometor 42 comprises a prism or grating 42a, slits 42b, and a photodetector 42c. The monochrometor 42 is set at a slit width and detecting wavelengths corresponding the elements to be measured. Detection signals obtained by the monochrometor 42 are amplified to a required level by the signal amplifier 43 and output from the signal amplifier 43. The output signals from the signal amplifier 43 are sent out to the data processing section of the computer 30 via an input/output interface 34. Conditions for analysis in the atomic absorption spectrophotometer are controlled by the computer 30.

Next, an explanation will be provided of a graphite atomizer section 32. A graphite furnace 1, which is a component of a heating furnace, is disposed on the optical axis 3 of the spectrophotometer. The graphite furnace 1 is heated by supplying an electric current to the furnace through an unillustrated electrode or the furnace itself directly by a power source 46. The power-supply operation by the power source 46 is controlled by the computer 30. Accordingly, the times at which the graphite furnace 1 is heated are appropriately set according to sample handling methods of various types of procedures which will be described later.

The automatic sampler section comprises a turntable 47 on which samples in a liquid state, standard samples, matrix modifiers, a blank solution are disposed, a syringe section 48 for weighing these solutions and a cleaning solution or the like, taking in or discharging them, a nozzle 2 for the above taking in or discharging, an arm 50 for supporting the nozzle 2, and an arm driver 50a for making the arm 50 rotate and move vertically in order to set the nozzle 2 to required positions. When the arm 50 is rotated by driving the arm driver 50a, the front end of the nozzle 2 moves along a track 63. As can be seen from the track 63, the tip of the nozzle 2 moves along predetermined places above a small in-take opening 1c of the graphite furnace 1, the cleaning tank 62, and the turntable 47.

Two pick-up positions 31 and 32 are formed on the track 63. These pick-up positions correspond to the two-container rows on the turntable 47. A row of sampling cups 51 is placed in the form of a circle on the outer circumference of the turntable 47. Placed in the form of a circle on the inner circumference of the turntable 47 are a plurality of containers 52 containing solutions of matrix modifiers corresponding to a plurality of elements to be tested, a plurality of containers 53 for containing standard sample solutions, a container 54 for containing a blank solution, and other necessary containers.

These containers and sampling cups are positioned at pick-up positions 31 and 32 at a desired time by a table driver 47a performing an indexing operation (a positioning operation) in accordance with a preset sequence. The operation of the table driver 47a is controlled by the computer 30.

A syringe section 48 comprises a cleaning tank 56 for containing a cleaning solution 55, a three-way selector valve 57, a milli-syringe 58 for supplying a cleaning solution, a pulse motor 59 for making the plunger of the milli-syringe move vertically, a micro syringe 60 for taking in or discharging various kinds of solutions on the turntable 47, and a pulse motor 61 for making the plunger of the micro syringe move vertically. A cleaning tank 62 for the nozzle 2 is disposed between the graphite furnace 1 and the turntable 47 on the track 63. Control signals are supplied to each of the following: the table rotation driver 47a, the arm driver 50a, and the pulse motors 59 and 61. Their operations are controlled by the computer 30.

Figure 3:
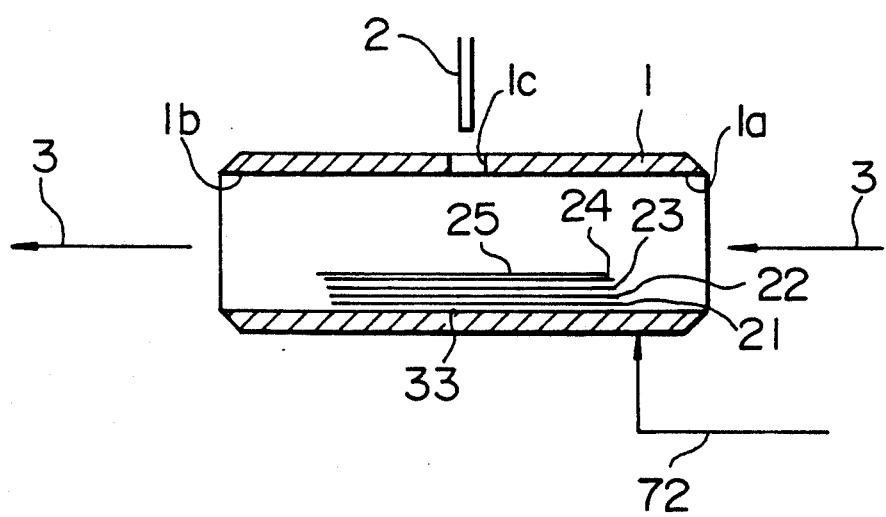
FIG. 3 is a view showing the layering of ingredients put into a graphite furnace.

As shown in FIG. 3, the graphite furnace 1 is formed in a tubular shape, both end sections of which are open. The small opening 1c into which the graphite furnace 1 can be entered is open in the vicinity of the center of the upper wall of the graphite furnace 1. A deposition zone 33 is formed in the lower wall of the graphite furnace 1. Various kinds of solutions added by the nozzle 2 can be received by the deposition zone 33. The deposition zone 33 is formed preferably with a slightly recessed depression. Power 72 is supplied from the power source 46 to the tubular furnace 1, so the furnace 1 will be heated.

Matrix modifiers are selected depending upon the kind of elements to be tested in a sample. For example, when an element to be tested is Fe or Co, Mg is used as a matrix modifier. When an element to be tested is Cu, Ag, or Se, a mixture of Pd and Mg is used as a matrix modifier. Other known matrix modifier combinations are as follows: Pd for Pb, La for Sn or Sc, Ca for B or P, Rh for Si, Mo for Ga, Ni for As, etc.

In the case of measurement operations in which the standard addition method is applied, a standard sample solution and a blank solution are put into the furnace 1. In the case of measurement operations in which the normal analytical curb method is applied, neither the standard sample solution nor the blank solution is used.

Next, the operation of an embodiment of the present invention will be explained with reference to FIGS. 2, 3 and 4. In this embodiment, an analysis apparatus shown in FIG. 1 is used and a standard addition method is used.

Figure 2:
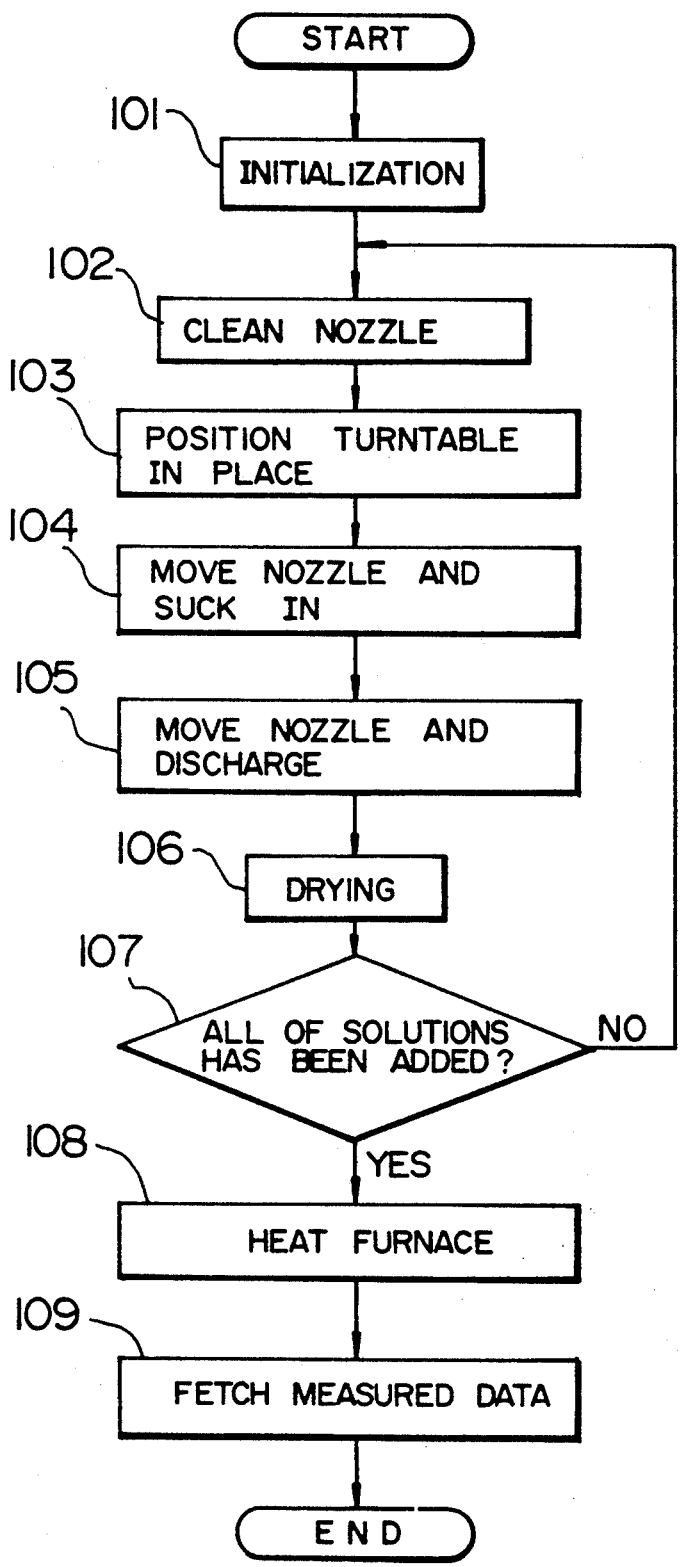
FIG. 2 is a flowchart showing the operation of the embodiment of the present invention.

The flowchart of FIG. 2 shows a case where a single sample is measured. By repeating the operations in FIG. 2, a large number of samples on the turntable 47 are measured one after another.

In step 101, first the analysis apparatus is initialized. At this time, the hollow cathode lamp 41 is lit, a slit width is set, and wavelengths to be received are set. The atomizer furnace 1 is not powered, and is maintained at the normal temperature. Then, the automatic sampler section operates.

In step 102, the inner and outer walls of the nozzle 2 are cleaned in the cleaning tank 62. In a state in which the nozzle 2 is dropped inside the cleaning tank 62, the inner wall of the nozzle 2 is cleaned by causing a cleaning solution from the syringe section 48 to be discharged from the opening in the front end of the nozzle 2; the outer wall of the nozzle 2 is cleaned by a cleaning solution with which the cleaning tank is filled by the above discharge. A discharge port is disposed in the bottom of the cleaning tank 62, thereby causing the cleaning solution which performed the cleaning in the cleaning tank 62 to be promptly discharged when the discharge of the cleaning solution from the nozzle 2 is completed.

In step 103, the table driver 47a operates so as to position a required container on the turntable 47 at the pick-up position 31 or 32. In this example, a container 52, as a first container, in which a matrix modifier solution is contained is rotated and moved to the pick-up position 32, and is stopped.

In step 104, the arm driver 50 is pivoted, causing the nozzle 2 which has been cleaned to be moved to the pick-up position 32. Then, the front end of the nozzle 2 is made to drop into the solution of the container 52 and the plunger of the micro syringe 60 is operated. Thus, a predetermined volume of matrix modifier solution is sucked into the nozzle 2.

In step 105, the arm 50 is moved upward and pivoted in order to move the nozzle 2 to above the small in-take opening 1c of the graphite furnace 1. Thereafter, by making the arm 50 move downward, the nozzle 2 is inserted into the furnace 1 through the small opening 1c. Next, by operating the plunger of the micro syringe 60, the matrix modifier solution held inside the nozzle 2 is discharged onto the deposition zone 33 of the furnace 1. As a result, first a layer of the matrix modifier is formed on the deposition zone 33. Thereafter, the arm 50 moves upward, causing the nozzle 2 to be pulled out of the furnace 1 and then to be transported to the cleaning tank 62.

In step 106, power is supplied to the graphite furnace 1 from the power supply 46, and the graphite furnace 1 is heated to a fixed temperature in a temperature range of 80° to 120° C. and heated for a fixed time of between 20 to 30 seconds. Thereafter, the supply of power to the furnace 1 is stopped, allowing the furnace 1 to cool.

In step 107, it is checked whether a required sampling operation depending upon objective elements to be tested or upon the kind of sample has been terminated. In the example shown in FIG. 2, because a sample solution must be added after a matrix modifier is added, the sequence returns from step 107 to step 102.

Next, to add a sample, steps 102 through 106 are performed. In step 103, the table driver 47a is operated to position a sampling cup 51 in which a sample to be analyzed is contained at the pick-up position 31. In step 104, a fixed amount of sample solution is sucked from this sampling cup into the nozzle 2.

Thereafter, the third time that the steps 102 to 106 are performed, the addition of the standard sample solution into the furnace 1 and drying are performed. On the fourth time that the steps 102 to 106 are performed, the addition of a blank solution and drying are performed. On the fifth time that the steps 102 to 106 are performed, the addition of an additional matrix modifier and drying are performed. Hence, if the entire pick-up station, including pick-up positions 31 and 32, is considered, the matrix modifier, the sample, the standard, blank, and the additional matrix modifier are, in this order, positioned at pick-up stations. As a result, the addition of the above into the atomizer furnace 1 is performed in the same order.

To shorten the whole analysis time, the drying operation of step 106 and the operation for cleaning the nozzle of step 102 should preferably be performed concurrently. On completion of a series of operations for sampling solutions in accordance with the sequence of programs stored in the computer 30, the computer 30 causes the power source 46 to feed power.

When it is judged to be "YES" in step 107, the process proceeds to step 108 where the graphite furnace 1 is heated to approximately 1000° C. and dried laminates or deposits inside the furnace 1 are ashed.

In step 109, power is supplied so that the atomizer furnace 1 is heated to a higher atomization temperature, and thus elements to be tested in a sample are atomized. The occurrence of atomized vapor of elements causes the intensity of light passing through the furnace 1 to decrease. Signals indicating variations in the intensity of light corresponding to the quantity of elements to be tested are taken in via a photodetector 42c and the amplifier 43 into the data processing section of the computer 30 where the concentration of elements in the sample is computed, and the results are output to an output device.

Figure 4:
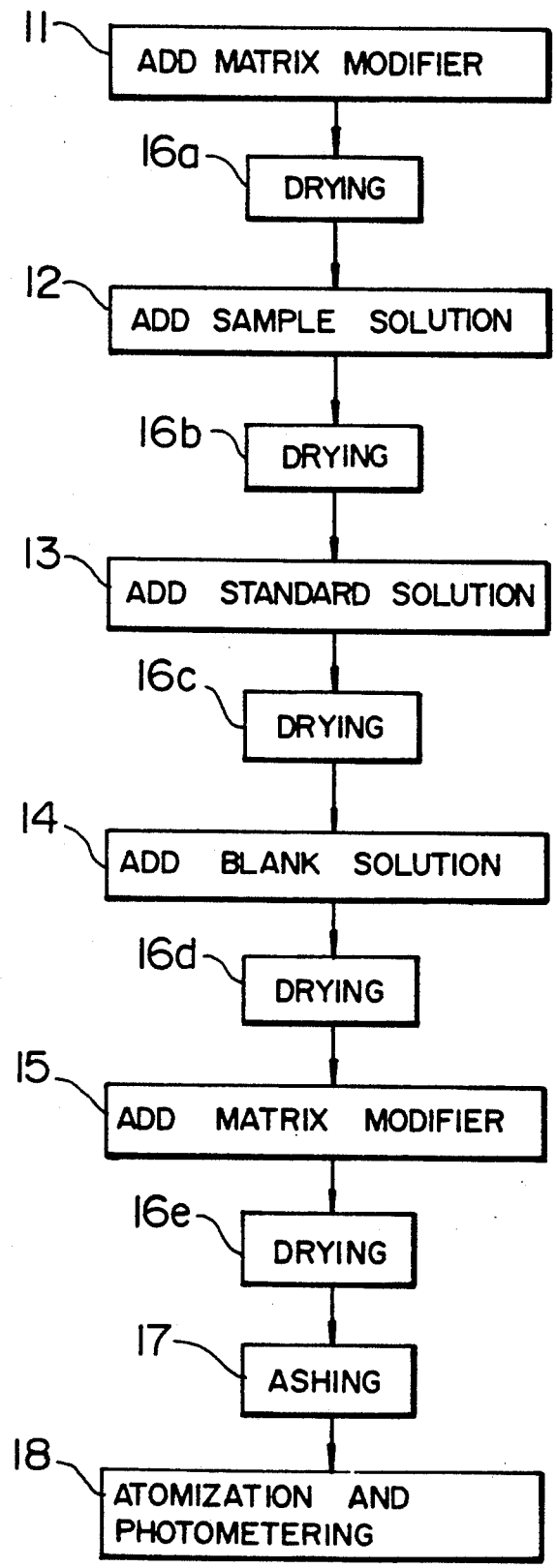
FIG. 4 is a sequential diagram of a sampling method.

FIG. 4 shows the operation performed with respect to the graphite furnace 1. The following steps are in turn performed: step 11: addition of a matrix modifier to the furnace 1; step 12: addition of a sample solution; step 13: addition of a standard solution; step 14: addition of a blank solution; and step 15: addition of an additional matrix modifier. Drying operations 16a to 16e are performed after each of the addition operations.

At the time the steps up to the drying operation 16e have been terminated, there is a laminated dried substance shown in FIG. 3 on the deposition zone 33 of the furnace 1. In FIG. 3, there is a matrix modifier layer 21 in the bottommost layer of the dried substance. Stacked thereon in turn are a sample layer 22, a standard layer 23, a blank layer 24, and an additional matrix modifier layer 25.

An ashing operation 17 performed after the drying operation 16e in FIG. 4 corresponds to step 108 in FIG. 2; an atomization and photometering operation 18 corresponds to step 109 in FIG. 2.

The following were determined by an experiment: repetitive reproducibility (A) for measurements based on the method shown in FIG. 2 and repetitive reproducibility (B) for a case where a mixed solution in which a sample and a matrix modifier are mixed by hand beforehand was measured. In this experiment, Pb (lead) was used as an element to be tested and palladium nitrate was used as a matrix modifier. Reproducibilities obtained by the experiment were expressed in a standard deviation factor, 0.8% in the case of (A) and 0.7% in the case of (B). Incidentally, the reproducibility when operations 12 through 18 were performed (excluding operations 11 and 16a in FIG. 4) had a standard deviation factor of 1.6%. Therefore, it can be understood that, if the present invention is applied, a sufficient reproducibility can be obtained even if a mixed solution of a sample and a matrix modifier is not prepared in advance.

Next, another embodiment of the present invention will be explained.

Although the analysis apparatus shown in FIG. 1 is used in the second embodiment, a point of difference with the first embodiment is that the graphite furnace 1 is maintained at a temperature of between 100° to 200° C. from the time when step 102 in FIG. 2 is started and to the time when step 107 is terminated. In step 101 for initialization, the supply of power to the graphite furnace 1 is started so that a drying temperature becomes lower than an ashing temperature. In this case, various kinds of solutions are discharged into the furnace 1 more gradually than in the first embodiment. Since the drying operation is performed on the deposition zone 33 of the furnace 1 while a solution is being added from the graphite furnace 1, if all of the required solutions have been completely added, it can be quickly heated to an ashing temperature. The order of the addition of various kinds of solutions is the same as in the first embodiment.

What is claimed is:

1. A sample handling method in which a sample and a matrix modifier are put into a furnace and elements to be tested in the sample are atomized in the furnace, comprising the steps of:

adding a matrix modifier into the furnace before the sample is put into the furnace; and adding an additional matrix modifier into the furnace after the sample has been added.

2. A sample handling method according to claim 1, wherein the sample is added in such a manner as to directly contact a layer of the matrix modifier which has been firstly added.

3. A sample handling method, comprising the steps of:
adding a sample and a matrix modifier into a furnace by a nozzle movable between a pick-up station and the furnace when the furnace is being maintained at a temperature lower than an ashing temperature at which the sample is ashed;
positioning a container in which a matrix modifier is contained, then a sampling cup in which a sample is contained, and again the container in which the matrix modifier is contained, at the pick-up station;
causing the nozzle to operate so that a first quantity of the matrix modifier, a quantity of the sample and a second quantity of the matrix modifier are supplied in this order from the pick-up station to the furnace; and
heating the furnace to the ashing temperature and then to an atomization temperature after the supply operation by the nozzle is terminated.

4. A sample handling method according to claim 3, wherein the addition of the sample to the furnace is performed after the first quantity of the matrix modifier received in the furnace is dried, and wherein the addition of the second quantity of the matrix modifier into the furnace is performed after the sample which has been received is dried.

5. A sample handling method, comprising:
a first step of adding a matrix modifier into a deposition zone in the furnace to form a layer of the matrix modifier;
a second step of adding a sample including elements to be tested onto the layer of the matrix modifier formed in the deposition zone;
a third step of adding an additional matrix modifier into the deposition zone after the sample is added; and
a fourth step of maintaining the furnace at such a high temperature as that at which the elements to be tested are atomized after the third step has been terminated.

6. A sample handling method according to claim 5, wherein a standard solution and a blank solution are added into the deposition zone after the second step, and thereafter the third step is performed.

7. A sample handling method, comprising the steps of:
adding a solution including a matrix modifier into a furnace into which a light beam from a light source can enter;
forming a dried layer of the matrix modifier by maintaining the furnace at a drying temperature;
adding a sample solution directly onto the layer of the dried layer of the matrix modifier;
causing the sample solution to be dried by maintaining the furnace at a drying temperature;
adding a solution including a matrix modifier onto a dried substance including the matrix modifier and the sample which have been previously added; and
atomizing elements to be tested in the sample in the furnace after all of ingredients in the furnace has been dried.

8. A sample handling method according to claim 7, wherein a drying operation is performed in parallel with the addition of the solution including the matrix modifier and the sample solution.

9. A sample handling apparatus equipped with a furnace which atomizes elements to be tested in a sample supplied thereunto, comprising:
a turntable including a sample cup in which a sample is contained and a container in which a matrix modifier solution is contained;
a nozzle for supplying said sample and said matrix modifier solution;
a pick-up station;
means for providing relative movement between said nozzle and said turntable;
means for heating said furnace;
means for controlling the relative movement providing means and said heating means so that said container is positioned in said pick-up station before and after said sample cup is positioned in said pick-up station while said furnace is maintained at a temperature lower than an ashing temperature;
means for supplying a quantity of the matrix modifier, a quantity of the sample, and an additional quantity of the matrix modifier in this order from the pick-up station into the furnace; and
means for heating the furnace to an atomization temperature through said ashing temperature after the supply operation has been terminated.

10. A sample handling apparatus according to claim 9, wherein the controlling means controls said heating means to heat the furnace to a temperature so that the sample supplied into the furnace is dried before the additional quantity of the matrix modifier is added.

11. A sample handling apparatus according to claim 9, wherein said means for providing relative movement further comprises:
means for rotating said turntable; and
means for moving said nozzle.

12. A sample handling apparatus according to claim 11, wherein said means for supplying a quantity of the matrix modifier includes said nozzle.

* * * * *